United States Patent [19]

Westley et al.

[11] 4,181,573
[45] Jan. 1, 1980

[54] PROCESS FOR THE PRODUCTION OF ANTIBIOTIC X-14547

[75] Inventors: John Westley, Clifton; Chao-Min Liu, Cedar Grove, both of N.J.

[73] Assignee: Hoffmann-La Roche Inc., Nutley, N.J.

[21] Appl. No.: 898,052

[22] Filed: Apr. 20, 1978

Related U.S. Application Data

[62] Division of Ser. No. 712,286, Aug. 6, 1976, Pat. No. 4,100,171.

[51] Int. Cl.$^2$ .............................................. C12D 9/00
[52] U.S. Cl. .................................... 435/119; 435/886
[58] Field of Search ..................................... 195/80 R

[56] References Cited
U.S. PATENT DOCUMENTS 4,100,171  7/1978  Westley et al. ................. 260/326.33

Primary Examiner—Raymond N. Jones
Assistant Examiner—Robert J. Warden
Attorney, Agent, or Firm—Jon S. Saxe; Bernard S. Leon; Frank P. Hoffman

[57] ABSTRACT

The invention relates to a new and useful antibiotic substance which is of the formula

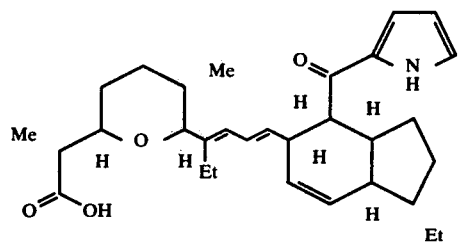

and to processes for its production and recovery. The antibiotic which exhibits ionophoric properties, is classified as a polyether group antibiotic. the antibiotic of formula I is effective in inhibiting the growth of gram positive bacteria and exhibits utility as an antihypertensive agent and as a compound to improve ruminant feed utilization. The antibiotic of Formula I is prepared by cultivating a strain of Streptomyces sp. X-14547 in an aqueous carbohydrate solution containing nitrogenous nutrients and mineral salts and thereafter isolating the antibiotic from the fermentation broth.

1 Claim, 1 Drawing Figure

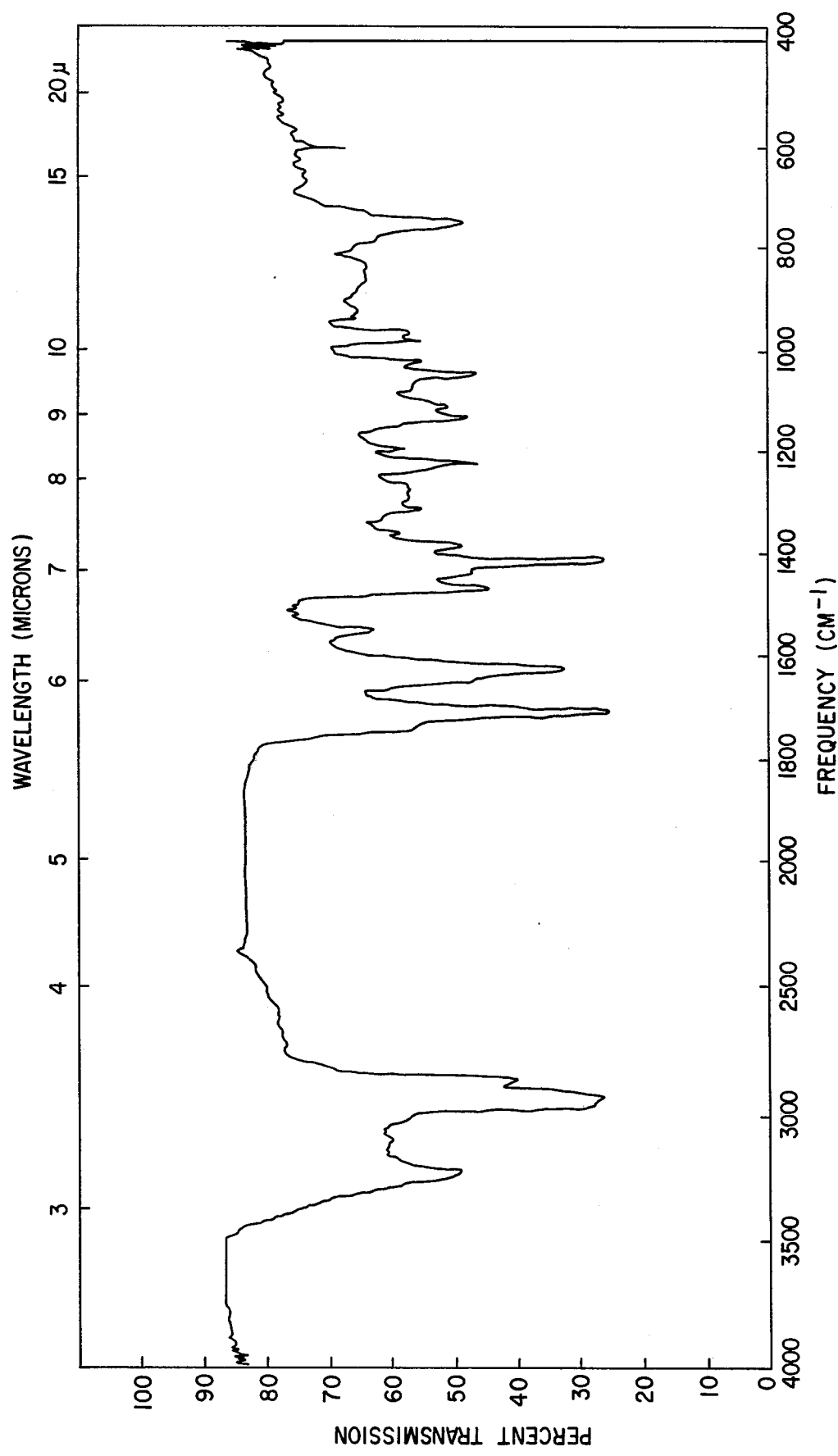

PROCESS FOR THE PRODUCTION OF ANTIBIOTIC X-14547

This is a division of application Ser. No. 712,286, filed Aug. 6, 1976 now U.S. Pat. No. 4,100,171.

DESCRIPTION OF THE INVENTION

There is provided according to the present invention an antibiotic substance effective in inhibiting the growth of gram-positive bacteria which is of the formula

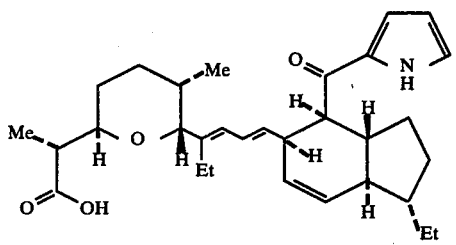

wherein Me is methyl and Et is ethyl.

Chemically, this substance is known as α-(R), 5 (S)-dimethyl-6(R)-{1-ethyl-4-[4-(R)-(2-pyrrolyl-carbonyl)-1(S)-ethyl-3a(R),4,5(R),7a(R)-tetrahydroindan-5-yl]-1(E), 3(E)-butadienyl}tetrahydropyran-2-acetic acid.

There is further provided according to the present invention, a fermentation process for the production of such antibiotic substance together with the isolation techniques utilized to recover the compound of Formula I from the fermentation broth.

The organism producing the antibiotic of the present invention is a new species designated Streptomyces sp. X-14547. A culture of the living organism, given the laboratory designation X-14547 has been deposited in the U.S. Department of Agriculture, Agriculture Research Service, NRRL, Peoria, Illinois and added to its permanent collection of microorganisms as NRRL 8167. The culture has been identified as a strain of *Streptomyces antibioticus.*

The new microorganism was isolated from a soil sample collected at Martinsville, Virginia. The representative strain of Streptomyces sp. X-14547 has the following characteristics:

GENERAL CHARACTERISTICS

Streptomyces X-14547 produces a substrate mycelium which does not fragment into spores, and an aerial mycelium which forms rectus-flexibilis chains of spores; the spores have a smooth surface. The spores are 1.26 to 1.42 μin length and 0.69 to 0.91 μ in width. The cell wall contains an isomer of diaminopimelic acid other than the meso form: This fact as well as the above colony characteristics place this culture in the genus Streptomyces.

GROWTH CHARACTERISTICS

The standard ISP media set forth in Shirling and Gottlieb, "Methods for Characterization of Streptomyces Species", Intern, J. System. Bacteriol., 16, pp 313–400, 1966, as well as various other media used to characterize the culture are listed below:
  ISP-1 through ISP-9 are described by Shirling and Gottlieb in above article.
  Czapek-Dox: Czapek-Dox Broth (BBL) to which 1.5% agar was added.
  Bennett's: Yeast extract, 0.1%; beef extract, 0.1%; N-Z Amine A (casein hydrolysate from Sheffield, Inc.), 0.2%; dextrose, 1% agar, 1.8% pH 7.3.
  Sabouraud Dextrose Agar: (Difco).
  Thermoactinomyces Fermentation: Bacto Thermoactinomyces fermentation medium (Difco) to which 1.5% agar was added.
  ATCC 5: Sporulation agar: Yeast extract, 0.1%; beef extract, 0.1%; tryptose, 0.2%; $FeSO_4$, trace; glucose, 1.0%; agar, 1.5%; pH 7.2.
  Amidex: Amidex (Corn Products Co., Decatur, Ill.) 1%; N-Z Amine A, 0.2%; beef extract, 0.1%; yeast extract, 0.1%; $CaCl_2.2H_2O$, 0.0014%; agar, 2%; pH 7.3.
  Starch casein: soluble starch, 1%; casein, 0.1%; $K_2HPO_4$, 0.05%; $MgSO_4$, 0.05%; agar, 1.5%; pH 7.4.

Table 1 below describes the amount of growth, degree of sporulation, spore mass color, and color of the reverse substrate mycelium. Agar plates were read after 14 days of incubation at 28° C. The color scheme used was the Color Harmony Manual Fourth edition, 1958 (Container Corp. of America).

Table 1

| Cultural Characteristics of Streptomyces sp. X 14547 | | | |
| --- | --- | --- | --- |
| Agar Medium | Amount of Growth Degree of Sporulation | Spore Mass Color | Color of Reverse Substrate Mycelium |
| Yeast Malt Extract (ISP-2) | moderate to abundant growth; well sporulated; slightly hygroscopic | 3 fe (silver gray) mostly; some tufts of a (white) | 2 nl (covert brown) at center; 2 ca (light ivory) at edge |
| Oatmeal (ISP-3) | abundant growth; well sporulated | 3 fe (silver gray) | 3 fe (silver gray) at center and 2 dc (natural) at edge |
| Inorganic Salts Starch (ISP-4) | abundant growth; well sporulated | 3 fe (silver gray); with edges and flecks of b (oyster white) | 2 dc (natural) |
| Glycerol Asparagine (ISP-5) | moderate growth; moderately to well sporulated; slightly hygroscopic | 2 fe (covert gray) with patches and edge of b (oyster white) | 2 ec (bisquit) mostly; 2 ge (covert tan) at edge |
| Peptone Yeast Extract Iron (ISP-6) | moderate growth; no sporulation; dark brown soluble pigment | i (gray) where not sporulated | i (gray) where not sporulated |
| Tyrosine | poor growth; some | 2 dc (natural) | 3 li (beaver) |

Table 1-continued

| Agar Medium | Amount of Growth Degree of Sporulation | Spore Mass Color | Color of Reverse Substrate Mycelium |
|---|---|---|---|
| (ISP-7) | sporulation; slight amount of brown soluble pigment | | |
| Czapek-Dox | poor growth; sparsely sporulated | b (oyster white) | b (oyster white) |
| Bennett's | moderate growth; well sporulated; hygroscopic | 2 fe (covert gray) | 3 lg (adobe brown) |
| Sabouraud Dextrose | moderate growth; no sporulation | 3 ie (camel) where not sporulated | 3 ie (camel) where not sporulated |
| Thermoactinomyces Fermentation | abundant growth; well sporulated; hygroscopic | 3 fe (silver gray) mostly; with tufts of b (oyster white) | 3 pn (dark brown) at center; and 3 ng (yellow maple) at edge |
| ATCC medium 5 (American Type Culture Collection Catalogue of Strains. 12th Ed. 1976. Rockville, Md.) | moderate growth; well sporulated; groscopic | 3 fe (silver gray); also areas of 3 dc (natural) | 3 pl (mustard brown) |
| Amidex | abundant growth; well sporulated; slightly hygroscopic | 3 fe (silver gray) mostly; edges of b (oyster white) | 3 pl (mustard brown) at center; 2 cb (ivory tint) around edge |
| Starch Casein | abundant growth; well sporulated; hygroscopic | 3 fe (silver gray); b (oyster white) in one area | 2 dc (natural) |

Table 2 below sets forth the morphological and physiological characteristics of Streptomyces sp. X-14547.

Table 2

Morphological and Physiological Characteristics of Streptomyces sp. X-14547

| Test | Response of Culture X-14547 |
|---|---|
| Chromagenic reaction, ISP-6 | + |
| Melanin, ISP-7 | + weak |
| Spore surface | smooth |
| Color of spore mass | gray |
| Spore chain form | rectus-flexibilis |
| D-Glucose utilization | + + |
| D-Xylose utilization | + + to + |
| L-Arabinose utilization | + + |
| L-Rhamnose utilization | + + |
| D-Fructose utilization | + + |
| D-Galactose utilization | + + |
| Raffinose utilization | − |
| D-Mannitol utilization | + + |
| i-Inositol utilization | + + |
| Salicin utilization | − |
| Sucrose utilization | − |
| Cellulose utilization | − |
| Reverse side pigment | − |
| Soluble pigment | − |
| Streptomycin sensitivity, 10 μg disc | + |
| Nitrate reduction | − |
| Casein hydrolysis | + |
| Gelatin hydrolysis | + |
| Starch hydrolysis | + |
| ISP-1 darkening | + |
| NaCl (%) tolerance | 5 |
| Temperature growth range °C. | 10–37 |
| DAP isomer | Other than the MESO isomer |

+ + = strong positive response; − = negative response

According to R. E. Buchanan and N. E. Gibbons, "Bergey's Manual of Determinative Bacteriology, 8th edition, 1974, Williams and Wilkins Co., Baltimore, Md., culture X-14547 is similar to Streptomyces antibi- otics but when the two were compared there were differences noted in utilization of L-arabinose, melanin production on ISP-7, and reduction of nitrate.

The species Streptomyces X-14547 described herein includes all strains of Streptomyces which form a compound of the Formula I and which cannot be definitely differentiated from the culture number X-14547 and its subcultures including mutants and variants. The compound of the Formula I is identified herein and after this identification is known, it is easy to differentiate the strains producing a compound of the Formula I from others.

Streptomyces sp. X-14547, when grown under suitable conditions, produces a compound of the Formula I. A fermentation broth containing Streptomyces sp. X-14547 is prepared by inoculating spores or mycelia of the organism producing the compound of the Formula I into a suitable medium and then cultivating under aerobic conditions. For the production of a compound of the Formula I, cultivation on a solid medium is possible but for production in large quantities, cultivation in a liquid medium is preferable. The temperature of the cultivation may be varied over a wide range, 20°–35° C., within which the organism may grow but a temperature of 26°–30° C. and a substantially neutral pH are preferred. In the submerged aerobic fermentation of the organism for the production of a compound of the Formula I, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of a compound of the Formula I.

The following Examples will serve to illustrate this invention without limiting it thereto.

EXAMPLE 1

Tank fermentation of Streptomyces sp. X-14547

The antibiotic X-14547 producing culture is grown and maintained on an Amidex agar slant having the following composition (grams/liter distilled water):

|  |  |
|---|---|
| Amidex | 10.0 |
| N-Z amine A | 2.0 |
| Beef extract | 1.0 |
| Yeast extract | 1.0 |
| $CoCl_2 \cdot 6H_2O$ | 0.02 |
| Agar | 20.0 |

The slant is inoculated with antibiotic X-14547 producing culture and incubated at 28° C. for 7–10 days. A chunk of the agar containing spores and mycelia from the sporulated culture slant is then used to inoculate a 6-liter Erlenmeyer flask containing 2 liters of sterilized inoculum medium having the following composition (grams/liter distilled water):

|  |  |
|---|---|
| Tomato pomace solids | 5.0 |
| Distiller's dried solubles | 5.0 |
| OM peptone | 5.0 |
| Debittered yeast | 5.0 |
| Corn starch | 20.0 |
| $CaCO_3$ | 1.0 |
| $K_2HPO_4$ (anhydrous) | 1.0 |

Adjust pH to 7 with NaOH before autoclaving at 15–20 pound pressure for 45 minutes.

The inoculated inoculum medium is incubated at 28° C. for 72 hours on a rotary shaker, operating at 250 rpm with a 2-inch stroke.

A four liter portion of the resulting culture is then used to inoculate 60 gallons in a 100 gallon fermentor having the following composition (grams/liter distilled water):

|  |  |
|---|---|
| Glucose | 10.0 |
| Edible molasses | 20.0 |
| HySoy T | 5.0 |
| $CaCO_3$ | 2.0 |

Adjust pH to 7.2 with NaOH before sterilization for 1¼ hours with 60 lb./in² steam.

The inoculated medium is aerated with sterilized compressed air at a rate of 3 cubic feet per minute and is stirred with agitators at 280 rpm. The fermentation is carried out at 28° C. for 4–6 days.

EXAMPLE 2

Isolation of antibiotic X-14547 and co-metabolites 3-ethyl-1,3-dihydro-3-methoxy-2H-indole-2-one and pyrrole-2-carboxylic acid Step A. To the whole broth from a 100 gallon (380 liters) fermentation as set forth in Example 1 was added, after 4–6 days of growth, an equal volume of ethyl acetate. After stirring for one hour the solvent layer was separated and concentrated to 2 liters under reduced pressure. The concentrated solvent extract was washed with equal volumes of 1N HCl three times. The solvent was dried over anhydrous $Na_2SO_4$ and concentrated to an oil under reduced pressure. The oil was dissolved in diethyl ether and crude pyrrole-2-carboxylic acid crystals were separated by filtration. Recrystallization from ethanol/ether yielded the analytical sample of the above compound: mp 202°–203° C.

microanalysis: calcd for $C_5H_5NO_2$ (111.10): calcd %C, 54.06; %H; 4.54; %N, 12.60. found %C, 54.33; %H, 4.65; %N, 12.60.

Step B. The mother liquor was concentrated to an oil under reduced pressure, redissolved in 250 ml of acetonitrile and washed twice with equal volumes of n-hexane. The hexane washes were pooled and extracted with ½ volume of methanol. The methanol extract was pooled with the acetonitrile and the solvent removed under reduced pressure. The oily solid was dissolved in acetonitrile and after cooling to approximately 3° C. overnight crystalline antibiotic X-14547 was recovered upon filtration as a hemihydrate, mp 137° C., $[\alpha]_D -285°$ (C, 1 in $CHCl_3$).

microanalysis: calcd for $C_{31}H_{43}NO_4 \cdot (H_2O)_{0.5}$ (502.70): %C, 74.07; %H, 8.82; %N, 2.78; %O; 14.32. found: %C, 74.36; %H, 8.93; %N, 2.50; %O, 13.81.

Step C. The $CH_3CN$ mother liquor was concentrated to an oily solid and subjected to chromatography on a hexane slurry packed 600 g silica gel (Davison grade 62) column. The column was eluted with 250 ml of hexane and then a gradient between 1 liter of 2% ethyl acetate in hexane to 1 liter of ethyl acetate/hexane (3:1) and then 500 ml of ethyl acetate. Fractions of 6 ml each were collected and from fraction numbers 100 to 200 subsequent to the solvent being removed under reduced pressure, additional antibiotic X-14547 was recovered. From fractions 201 to 290 after concentration and crystallization from acetonitrile, 3-ethyl-1,3-dihydro-3-methoxy-2H-indole-2-one was recovered. mp 179° microanalysis calcd: for $C_{11}H_{13}NO_2$ (191.23): calcd: %C, 69.09; %H, 6.85; %N, 7.33. found: %C, 69.02; %H, 6.96; %N, 7.19.

EXAMPLE 3

Tank fermentation of antibiotic X-14547

The antibiotic X-14547 producing culture is grown and maintained on an Amidax agar slant as described in Example 1 or on a starch-casein agar slant having the following composition (grams/liter distilled water):

|  |  |
|---|---|
| Soluble starch | 10.0 |
| Casein | 1.0 |
| $K_2HPO_4$ (anhydrous) | 0.5 |
| $MgSO_4$ (anhydrous) | 0.5 |
| Agar | 20.0 |

Adjust pH to 7.4 with NaOH before autoclaving at 15–20 p.s.i. for twenty minutes.

The slant is inoculated with antibiotic X-14547 producing culture (Streptomyces sp. X-14547) and incubated at 28° C. for 7–10 days. A chunk of agar from the sporulated culture is then used to prepare vegetative inoculum by inoculating a 6-liter Erlenmeyer flask containing 2 liters of sterilized inoculum medium having the following composition (grams/liter distilled water):

| | |
|---|---|
| Tomato pomace solids | 5.0 |
| Distiller's dried solubles | 5.0 |
| OM peptone | 5.0 |
| Debittered yeast | 5.0 |
| Corn starch | 20.0 |
| $CaCO_3$ | 1.0 |
| $K_2HPO_4$ (anhydrous) | 1.0 | pH is adjusted to 7.0 before autoclaving at 15–20 p.s.i. for forty-five minutes.

The inoculated inoculum medium is incubated for 72 hours at 28° C. on a rotary shaker operating at 250 rpm with a 2-inch stroke.

Four liters of this culture are used to inoculate 60 gallons of the following medium in a 100 gallon fermentor (grams/liter tap water):

| | |
|---|---|
| Tomato pomace solids | 5.0 |
| Distiller's dried solubles | 5.0 |
| OM peptone | 5.0 |
| Debittered yeast | 5.0 |
| Corn starch | 20.0 |
| $CaCO_3$ | 1.0 |
| $K_2HPO_4$ (anhydrous) | 1.0 |
| Sag 4130 Antifoam (Union carbide) | 0.1 |

The pH of the medium is adjusted to 7.0 with NaOH before sterilization for 1¼ hours with 60 p.s.i. steam.

The inoculated medium is aerated with compressed air at a rate of 3 cubic feet per minute and is stirred with agitators at 280 rpm. The fermentation is carried out at 28° C. for 43 hours.

Five gallons of this culture are used to inoculate 350 gallons of the following medium in a 1000 gallon tank utilizing the following medium (grams/liter tap water):

| | |
|---|---|
| Tomato pomace solids | 5.0 |
| Distiller's dried solubles | 5.0 |
| OM peptone | 5.0 |
| Dibittered yeast | 5.0 |
| Corn starch | 20.0 |
| $CaCO_3$ | 1.0 |
| $K_2HPO_4$ (anhydrous) | 1.0 |
| Sag 4130 Antifoam (Union carbide) | 0.1 |

The pH of the medium is adjusted to 7.0 with NaOH before sterilization for 1¼ hours with 60 p.s.i.[2] steam.

The inoculated medium is aerated with compressed air at a rate of 3 cubic feet per minute and is stirred with agitators at 280 rpm. The fermentation is carried out at 28° C. for 118 hours.

Isolation of antibiotic X-14547 and co-metabolites-3-ethyl-1,3-dihydro-3-methoxy-2H-indole-2-one and pyrrole-2-carboxylic acid Step A. To the whole broth from a 350 gallon (1350 liters) fermentation as set forth in Example 2 was added, after 118 hours of growth, an equal volume of ethyl acetate. After stirring for one hour the solvent layer was separated and concentrated to 7.25 liters under reduced pressure. The concentrated solvent extract was washed with 3 liters of 1 N HCl three times. The solvent was dried over anhydrous $Na_2SO_4$ and concentrated to an oil under reduced pressure. The oil was dissolved in diethyl ether and crude pyrrole-2-carboxylic acid crystals were separated by filtration. Recrystallization from ethanol/ether yielded the analytical sample of the above compound: mp 202°–203° C.

Microanalysis: calcd for $C_5H_5NO_2$ (111.10): calcd %C, 54.06; %H, 4.54; %N, 12.60. found %C, 54.33; %H, 4.65; %N, 12.60.

Step B. The mother liquor was concentrated to an oil under reduced pressure, redissolved in 1 liter of acetonitrile and washed twice with equal volumes of n-hexane. The hexane washes were pooled and extracted with ½ volume of methanol. The methanol extract was pooled with the acetonitrile and the solvent removed under reduced pressure. The oily solid was dissolved in acetonitrile and after cooling to approximately 3° C. overnight crystalline antibiotic X-14547 was recovered upon filtration as a hemihydrate, mp 137° C., $[\alpha]_D - 285°$ (C, 1 in $CHCl_3$).

Microanalysis: calcd for $C_{31}H_{43}NO_4 \cdot (H_2O)_{0.5}$ (502.70): %C, 74.07; %H, 8.82; %N, 2.78; %O, 14.32. found %C, 74.36; %H, 8.93; %N, 2.50; %O, 13.81.

Step C. The $CH_3CN$ mother liquor was concentrated to an oily solid and subjected to chromatography on a hexane slurry packed 600 g silica gel (Davison grade 62) column. The column was eluted with 1 liter of hexane and then a gradient between 4 liters of 2% ethyl acetate in hexane to 4 liters of ethyl acetate/hexane (3:1) and then 2 liters of ethyl acetate. Fractions of twenty five ml each were collected and from fraction numbers 100 to 200 subsequent to the solvent being removed under reduced pressure, additional antibiotic X-14547 was recovered. From fractions 201 to 290 after concentration and crystallization from acetonitrile, 3-ethyl-1,3-dihydro-3-methoxy-2H-indole-2-one was recovered, mp 179°

Microanalysis calcd for $C_{11}H_{13}NO_2$ (191.23): calcd: %C, 69.09; %H, 6.85; %N, 7.33. found: %C, 69.02; %H, 6.96; %N, 7.19.

EXAMPLE 5

Isolation of the sodium salt of antibiotic X-14547

The whole broth from another fermentation run was extracted with a one half volume of chloroform. The solvent layer was separated and concentrated under reduced pressure to 2.35 liters, and washed successively with equal volumes of 1 N HCl, 1 N NaOH and water. The solvent was dried over $Na_2SO_4$, and concentrated to an oil. The oil was redissolved in 2 liters of acetonitrile and washed with 2 liters of n-hexane. The acetonitrile was concentrated to an oil and filtered through 970 grams of silica gel with 4 liters of methylene chloride and then 8 liters of methylene chloride-acetone (1:1). The biologically active fraction was chromatographed on a 300 gram slurry packed (methylene chloride) silica gel column and eluted with a gradient between 7 liters of methylene chloride and 7 liters of methylene chloride-diethyl ether-ethanol (48:48:14). Fractions numbered 290–460 (twenty-five ml each) were pooled and concentrated to an oil. The oil was dissolved in a small amount of acetonitrile and with the addition of n-hexane the sodium salt of antibiotic X-14547 was recovered by filtration as a white powder, containing 1 mole of hexane.

Calcd. $C_{31}H_{42}N\ NaO_4 \cdot C_6H_{14}$ (599.83): %C, 74.09; %H, 9.08; %N, 2.34; %Na 3.83.

Found: %C, 74.00; %H, 8.86; %N, 2.10; %Na, 4.04.

EXAMPLE 6

Preparation of the thallium salt of antibiotic X-14547

A solution of 1.3 g of antibiotic X-14547 in ethyl acetate was first washed with 1NHCl, and then four times with an aqueous solution of thallium hydroxide. The solvent was separated and concentrated to a small volume under reduced pressure and after addition of $CH_3CN$-$C_2H_5OH$, crystalline thallium salt of antibiotic X-14547 was recovered, mp. 194°–195° C.

Calcd. $C_{31}H_{42}NO_4Tl$ (697.05): %C, 53.42; %H, 6.07; %N, 2.01; %Tl 29.32.

Found: %C 53.51; %H, 6.01; %N, 1.98; %Tl 28.96.

EXAMPLE 7

Preparation of the R-(+)-1-amino-1-(4-bromophenyl)-ethane salt of antibiotic X-14547

A solution of 493 mg (1 mmol) of antibiotic X-14547 in methylene chloride was added to a solution of 181 mg of R-(+)-1-amino-1-(4-bromophenyl)-ethane in methylene chloride. After addition of n-hexane and slow evaporation of solvent, the crystalline final product was recovered. Recrystallization from methylene chloride-hexane yielded crystals suitable for X-ray analysis, mp. 128°–131°.*

*The crystalline salt (Example 7) contained two molecules of antibiotic X-14547 to one molecule of the amine, thus explaining the formula used to calculate the microanalysis. (analagous to antibiotic X-14547 hemihydrate in Example 3)

Calcd. $C_{70}H_{96}BrN_3O_8$ (1187.46): %C, 70.70; %H, 815; %N, 3.54; %Br, 6.73.

Found: %C, 70.96; %H, 8.30; %N 3.68; %Br, 6.83. Temperatures disclosed in this specification are in degrees celcius.

The following are various physical characteristics of antibiotic X-14547:

The infrared absorption spectrum of antibiotic X-14547 in a KBR pellet is shown in FIG. 1. The antibiotic exhibits characteristics absorption in the infrared region of the spectrum at the following wave lengths expressed in reciprocal centimeters:

Peaks occurred inter alia at 3140 (OH), 2740–2400 (carboxyl OH), 1735, 1710 (C=O), 1650 (conjugated C=O) and 1627 cm$^{-1}$ (conjugated C=C).

Antibiotic X-14547 exhibits an oral toxicity (LD$_{50}$) in mice of 129 mg/kg (24 hours).

Antibiotic X-14547 has exhibited antimicrobial activity against a variety of gram-positive bacteria and mycobacterium as indicated in Table 3 below.

Table 3

| Name of Organism | Culture Collection No. ATCC | NRRL | Antimicrobial activity of Antibiotic X-14547. Minimum inhibitory concentration* in Mcg/Ml |
|---|---|---|---|
| Bacillus megaterium | 8011 | | 0.1 |
| Sarcina lutea | 9341 | | 0.1 |
| Bacillus species E | 27859 | | 0.2 |
| Bacillus subtilis | | 558 | 0.1 |
| Staphylococcus aureus | 6538P | | 0.2 |
| Bacillus species TA | 27860 | | 0.2 |
| Mycobacterium phlei | 355 | | 3.1 |

Table 3-continued

| Name of Organism | Culture Collection No. ATCC | NRRL | Antimicrobial activity of Antibiotic X-14547. Minimum inhibitory concentration* in Mcg/Ml |
|---|---|---|---|
| Streptomyces cellulosae | 3313 | | 0.8 |
| Paecilomyces varioti | 26820 | | 6.3 |

*Lowest two-fold dilution giving a zone of inhibition in an agar well diffusion assay.

It has also been found and should be considered a part of the present invention that the novel 3-ethyl-1,3-dihydro-3-methoxy-2H-indole-2-one co-metabolite also exhibits antimicrobial activity against a variety of microorganisms as indicated in Table 4 below.

Table 4

| Name of Organism | Culture Collection No. ATCC | M.I.C.* in mcg/ml |
|---|---|---|
| Escherichia coli | 27856 | 5.0 |
| Pseudomonas aeruginosa | 8709 | 5.0 |
| Klebsiella pneumoniae | 27858 | 5.0 |
| Staphylococcus aureus | 6538P | 5.0 |
| Bacillus sp. TA | 27860 | 2.5 |
| Paecilomyces varioti | 26820 | 2.5 |

*Minimum inhibitory concentration per ml. in mcg.

As indicated above, antibiotic X-14547 and its salts together with its co-metabolite 3-ethyl-1,3-dihydro-3-methoxy-2H-indole-2-one possesses the property of adversely affecting the growth of certain gram-positive bacteria. They are useful in wash solutions for sanitary purposes as in the washing of hands and the cleaning of equipment, floors or furnishings of contaminated rooms or laboratories.

Antibiotic X-14547 has also been found to improve ruminant feed utilization, i.e., improve the digestive efficiency of certain herbivorous animals, for example, cattle. A discussion of the mechanism whereby feed is digested, degraded and metabolized in a ruminant animal can be found in U.S. Pat. No. 3,839,557 issued Oct. 1, 1974 which discloses the use of certain antibiotics in improving ruminant feed utilization and is incorporated herewith by reference. Economically-important ruminant animals are cattle, sheep and goats.

The effectiveness of antibiotic X-14547 in modifying the ratio of volatile fatty acids produced in the rumen (and thereby improve ruminant feed utilization) is demonstrated by means of the following in vitro testing.

Rumen fluid is obtained from a steer with a fistulated rumen. The steer is maintained on the following ration:

| Corn | 89.93% |
|---|---|
| Alfalfa meal | 5.000% |
| Soy bean oil meal | 3.00% |
| Limestone | 0.80% |
| NaCl | 0.60% |

| Dicalcium phosphate | 0.50% |
|---|---|
| Trace minerals | 0.025% |
| Vitamin premix additions | 0.1% |
| Vitamin A, TIU | 4.0003 |
| Vitamin D$_3$, IU | 0.801 |
| Vitamin E, TIU | 3.002 |

The rumen fluid is immediately strained through a #30 mesh sieve. For each fermentation, 75 ml of the resulting fluid is added to a 250 ml flask containing the following:

- 1 g of 80%:20% finely ground grain: hay ration;
- 1 ml of an 18% aqueous glucose solution (1 millimole per flask);
- 1.5 ml of a 3.1% aqueous urea solution (0.76 millimole per flask);
- 60 micromoles of each of the 10 essential amino acids (arginine, histidine, leucine, methionine, threonine, valine, lysine, isoleucine, phenylalanine, tryptophan);
- 1 ml of an aqueous solution of test drug to give either 10 or 25 μg/ml (calculated total volume of fermentation mixture of 80 ml); Each flask is incubated at 38° C. in a shaking water bath equipped with a gassing hood. Carbon dioxide is continuously passed through the hood. After four hours incubation, a 10 ml quantity of the fermentation fluid is centrifuged at 14,000 rpm (approximately 30,000 xg) for 20 minutes in an International Centrifuge equipped with a No. 874 angle head. Three ml of the supernate is added to 1 ml of a 25% metaphosphoric acid solution containing 23 micromoles 2-methyl valeric acid as an internal standard. The resulting fluid is permitted to sit at room temperature for 30 minutes. The fluid is filtered through a 0.22 millimicron Millipore filter and refrigerated until gas-liquid chromatographic analyses for volatile fatty acids.

Gas-liquid chromatographic (GLC) analyses of four in vitro control fermentations and two fermentations each with 10 and 25 ppm Antibiotic X-14547 are set forth in the following table.

Ratios of moles of propionate ($C_3$) to acetate ($C_2$) plus n-butyrate ($nC_4$) in in vitro rumen fermentations

| Description (Incubation Time) | μmoles $C_3$/μmoles $C_2$ + μmoles $nC_4$ | |
|---|---|---|
| | Replicate fermentations | Means (± 1σ) |
| Controls (0 hrs.) | 0.372 | |
| | 0.361 | |
| | 0.364 | |
| | 0.350 | 0.362 (± 0.009) |
| Controls (4 hrs.) | 0.393 | |
| | 0.337 | |
| | 0.427 | |
| | 0.388 | 0.386 (± 0.037) |
| Antibiotic X-14547 (4 hrs.), 10 ppm | 0.493 | 0.491 |
| | 0.489 | |
| Antibiotic X-14547 (4 hrs.) 25 ppm | 0.531 | 0.521 |
| | 0.510 | |

As shown in the above table the ratio of propionate ($C_3$) to acetates and n-butyrates is significantly improved. With the increase of propionates rather than acetates from the carbohydrates, the efficiency of carbohydrate and therefore feed utilization is increased.

Administration of antibiotic X-14547 hereafter "Antibiotic" or "Antibiotic Compound" prevents and treats ketosis as well as improves feed utilization. The causative mechanism of ketosis is a deficient production of propionate compounds. A presently recommended treatment is administration of propionic acid or feeds which preferentially produce propionates. It is obvious that encouraging propionate production from ordinary feeds will reduce incidence of ketosis.

It has been found that antibiotic X-14547 increases the efficiency of feed utilization in ruminant animals when it is administered orally to the animals. The easiest way to administer the antibiotic is by mixing it in the animal's feed.

However, the antibiotic can be usefully administered in other ways. For example, it can be incorporated into tablets, drenches, boluses, or capsules, and dosed to the animals. Formulation of the antibiotic compound in such dosage forms can be accomplished by means of methods well known in the veterinary pharmaceutical art.

Capsules are readily produced by filling gelatin capsules with any desired form of the desired antibiotic. If desired, the antibiotic can be diluted with an inert powdered diluent, such as a sugar, starch, or purified crystalline cellulose in order to increase its volume for convenience in filling capsules.

Tablets of the antibiotics are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly-used absorbents again include starch and lactose while magnesium carbonate is also useful for oily substances. Frequently-used binders are gelatin, gums, starch, dextrin and various cellulose derivatives. Among the commonly used lubricants are magnesium stearate, talc, paraffin wax, various metallic soaps, and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic. A substance such as iron filing is added to raise the density of the bolus and keep it static on the bottom of the rumen.

Dissolution of the antibiotic is delayed by use of a matrix of insoluble materials in which the drug is inbedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotic can be prepared in nonsolvents such as vegetable oils such as peanut, corn, or sesame oil, in a glycol such as propylene glycol or a polyethylene glycol; or in water, depending on the form of the antibiotic chosen.

Suitable physiologically acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend the antibiotic. For example, lecithin, alkylphenol oxide adducts, naphthalenesulfonates, alkylbenzesulfonates, and the polyoxyethylene sorbitan esters are useful for making suspensions in liquid nonsolvents.

In addition many substances which effect the hydrophilicity, density, and surface tension of the liquid can assist in making suspensions in individual cases. For example, silicone anti-foams, glycols, sorbitol, and sugars can be useful suspending agents.

The suspendable antibiotic may be offered to the grower as a suspension, or as a dry mixture of the antibiotic and adjuvants to be diluted before use.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be medicated with the antibiotic compounds, including common dry feeds, liquid feeds, and pelleted feeds.

The methods of formulating drugs into animal feeds are well known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

All of the methods of formulating, mixing and pelleting feeds which are normally used in the ruminant feed art are entirely appropriate for manufacturing feeds containing the antibiotic compound.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum since it would be expected that a beneficial change in the propionate/acetate ratio would occur upon oral administration of the instant antibiotic. Horses, swine and rabbits are exemplary animals which digest a part of their food by cecal fermentation.

Antibiotic X-14547 also exhibits activity in the treatment of hypertension in warm-blooded animals.

Antihypertensive activity is tested for in the DOCA-Na Sprague Dawley (Charles River) male rats weighing 170–210 grams. DOCA-Na hypertension is produced by unilateral nephrectomy followed by subcutaneous implantation of a 25 mg. desoxycortico sterone (DOCA) pellet. Animals are placed in individual cages receiving 0.9% sodium chloride solution and rat chow diet ad libitum. Two weeks are allowed to elapse from the time of surgery for development of hypertension, i.e., systolic blood pressure of at least 150 mm. Hg.

Systolic blood pressure and heart rate are measured indirectly from the tail of unanesthetized rats, using a pneumatic pulse transducer. Control readings are taken prior to drug and at 1, 3, 6 and 24 hours post drug.

The results are expressed as absolute values and percent changes from controls.

Table 4

| | DAY | RAT 1 | RAT 2 | RAT 3 | RAT 4 | RAT 5 | RAT 6 | MEAN | PCT CHANGE |
|---|---|---|---|---|---|---|---|---|---|
| SYSTOLIC BLOOD PRESSURE (mmHg) | | | | | | | | | |
| PRE DRUG CONTROLS | | 223 | 203 | 203 | 199 | 203 | 209 | 206.7 | |
| | | | | 10 MG/KG × 3 days PO | | | | | |
| POST DRUG VALUES IN (mmHg) | 1 | 216 | 178 | 184 | 198 | 151 | 203 | 188.3 | −9.0 |
| | 2 | 211 | 201 | 176 | 168 | 190 | 185.7 | −10.3 | |
| | 2 | 184 | 174 | 161 | 165 | 165 | 179 | 171.3 | −17.1 |
| | 3 | 214 | 195 | 193 | 219 | 198 | 211 | 205.0 | −0.7 |
| | 3 | 210 | 177 | 173 | 206 | 190 | 220 | 196.0 | −5.2 |
| | 4 | 197 | 172 | 229 | 212 | 179 | 228 | 202.8 | −1.7 |
| CARDIAC RATE (BEATS/MIN) | | | | | | | | | |
| PRE DRUG CONTROLS | | 440 | 360 | 460 | 410 | 400 | 400 | 411.7 | |
| | | | | 10 MG/KG × 3 days PO | | | | | |
| POST DRUG VALUES IN BEATS/MIN | 1 | 480 | 360 | 450 | 440 | 390 | 400 | 420.0 | 2.0 |
| | 2 | 430 | 320 | 360 | 490 | 370 | 430 | 400.0 | −2.6 |
| | 2 | 420 | 310 | 400 | 310 | 380 | 450 | 378.3 | −8.1 |
| | 3 | 380 | 360 | 360 | 360 | 370 | 350 | 363.3 | −11.3 |
| | 3 | 370 | 360 | 350 | 360 | 380 | 370 | 365.0 | −10.8 |
| | 4 | 370 | 320 | 360 | 350 | 340 | 400 | 356.7 | −13.1 |

For use as an anti-hypertensive agent, antibiotic X-14547 is formulated, using conventional inert pharmaceutical adjuvant materials, into dosage forms which are suitable for oral administration. Other dosage forms, e.g., parenteral, are possible but are not preferred. The oral dosage forms include tablets, capsules, dragees, suspensions, solutions and the like. The identity of the inert adjuvant materials which are used in formulating the active ingredients the active compounds into oral dosage forms will be immediately apparent to persons skilled in the art. These adjuvant materials, either inorganic or organic in nature, include, for example, gelatin, albumin, lactose, starch, magnesium stearate, preservatives (stabilizers) melting agents, emulsifying agents, salts for altering osmotic pressure, buffers, etc., which can be incorporated, if desired, into such formulations.

Generally the drug is administered once or twice a day.

The quantity of antibiotic X-14547 which is present in any of the above described dosage forms generally varies from 1 to 10 mg. per unit dosage. The dosage administered to a particular patient is variable, based on the weight of the patient and the condition of the patient. An effective dosage amount of active agent can, therefore, only be determined by the clinician utilizing his best judgement on the patient's behalf.

An example of a tablet formulation is as follows:

| Tablet Formulation | |
|---|---|
| | Per Tablet |
| Antibiotic X-14547 | 1.0 mg. |
| Lactose Anhydrous | 137.0 mg. |
| Corn Starch | 20.0 mg. |
| Microcrystalline Cellulose Ph 101 | 40.0 mg. |
| Magnesium Stearate | 2.0 mg. |
| | 200 mg. |

Procedure:
1. The drug was premixed with a part of the lactose, in a suitable mixer and thereafter milled.
2. The mixture was further blended with the cornstarch the remaining lactose and the cellulose for 15 minutes and thereafter milled.
3. The mixture was thereafter blended with the magnesium stearate for two minutes.
4. The tablets were compressed at a tablet weight of 200 mg using tablet punches having a diameter of approximately ¼ inch. The tablets may be either flat or biconnex and may be scored if desired.

1. A process for the production of the antibiotic X-14647 having the following formula

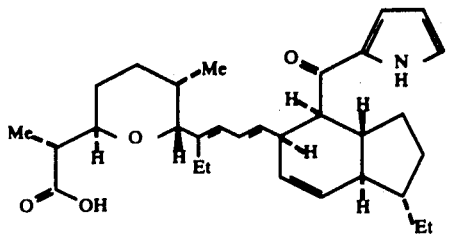

which comprises cultivating a strain of Streptomyces sp. X-14547, NRRL 8167, in an aqueous carbohydrate solution containing a nitrogenous nutrient under submerged aerobic conditions and thereafter isolating the X-14547 antibiotic from said solution.

* * * * *